United States Patent

Stöhr et al.

Patent Number: 4,988,803
Date of Patent: Jan. 29, 1991

[54] FIBER REACTIVE AZO DYES CONTAINING A MORPHOLINYL-, PIPERAZINYL- OR PIPERIDNYL- SUBSTITUTED FLUROTRIAZINYL RADICAL

[75] Inventors: Frank M. Stöhr, Odenthal; Hermann Henk, Cologne; Karl-Josef Herd, Odenthal, all of Fed. Rep. of Germany

[73] Assignee: Bayer Aktiengesellschaft, Leverkusen, Fed. Rep. of Germany

[21] Appl. No.: 462,918

[22] Filed: Jan. 5, 1990

Related U.S. Application Data

[63] Continuation of Ser. No. 212,826, Jun. 29, 1988, abandoned.

[30] Foreign Application Priority Data

Jul. 16, 1987 [DE] Fed. Rep. of Germany ....... 3723474
Oct. 3, 1987 [DE] Fed. Rep. of Germany ....... 3733571

[51] Int. Cl.$^5$ ..................... C09B 62/085; D06P 1/382
[52] U.S. Cl. .................................. 534/635; 534/582; 534/632; 534/638; 534/887
[58] Field of Search .................. 534/632, 635, 638

[56] References Cited

U.S. PATENT DOCUMENTS

| | | | |
|---|---|---|---|
| 3,627,749 | 12/1971 | Ackermann et al. | 534/632 |
| 4,446,067 | 5/1984 | Jager et al. | 534/638 |
| 4,473,499 | 9/1984 | Niwa et al. | 534/635 |
| 4,578,457 | 3/1986 | Seiler | 534/632 |

FOREIGN PATENT DOCUMENTS

| | | | |
|---|---|---|---|
| 0014844 | 9/1980 | European Pat. Off. | 534/635 |
| 0131545 | 1/1985 | European Pat. Off. | 534/638 |
| 227983 | 7/1987 | European Pat. Off. | 534/638 |
| 1274494 | 12/1961 | France | 534/638 |
| 872249 | 7/1961 | United Kingdom | 534/632 |
| 1566814 | 5/1980 | United Kingdom | 534/638 |
| 1569246 | 6/1980 | United Kingdom | 534/638 |
| 2055880 | 3/1981 | United Kingdom | 534/638 |

OTHER PUBLICATIONS

Abstract of Japanese Patent No. 60-36570.
Abstract of Japanese Patent No. 62-148473.
Abstract of Japanese Patent No. 55-102574.
Hensel et al., *Chemical Abstracts*, vol. 76, abstract No. 1288022, (1972).
Koch, W., *Chemical Abstracts*, vol. 99, Abstract No. 141483r, (1983).
Ramanathan et al., *Chemical Abstracts*, vol. 102, Abstract No. 8235a, (1985).
Tzikas et al., *Chemical Abstracts*, vol. 103, Abstract No. 143355a, (1985).
Yamanaka et al., *Chemical Abstracts*, vol. 104, Abstract No. 188371g, (1986).

Primary Examiner—Floyd D. Higel
Assistant Examiner—Fiona T. Powers
Attorney, Agent, or Firm—Sprung, Horn, Kramer & Woods

[57] ABSTRACT

An azo dyestuff of the formula

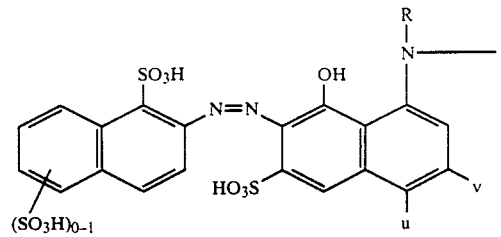

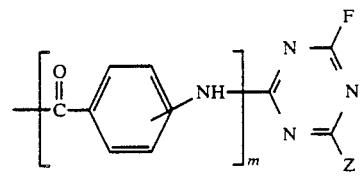

in which
u and v = H or $SO_3H$ and u ≠ v,
R = H, unsubstituted $C_1$–$C_4$-alkyl or $C_1$–$C_4$-alkyl substituted by OH, halogen, $SO_3H$ or $OSO_3H$,
m = 0 or 1 and

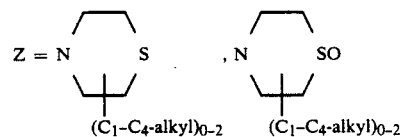

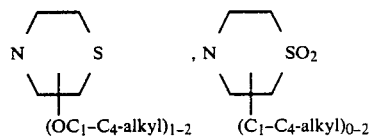

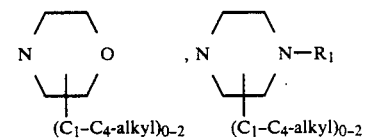

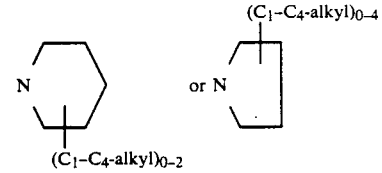

in which
$R_1$ = H, unsubstituted $C_1$–$C_6$-alkyl or $C_1$–$C_6$-alkyl substituted by OH, $OSO_3H$, $SO_3H$ or COOH. Such dye is particularly suitable for producing on cotton red dyeings and prints having excellent fiber-dyestuff bond stability, stability to oxidizing agents and wash-off properties.

7 Claims, No Drawings

FIBER REACTIVE AZO DYES CONTAINING A MORPHOLINYL-, PIPERAZINYL- OR PIPERIDNYL- SUBSTITUTED FLUROTRIAZINYL RADICAL

This application is a continuation, of application Ser. No. 212,826, filed 6/29/88, now abandoned.

The present invention relates to fibre-reactive azo dyestuffs of the formula

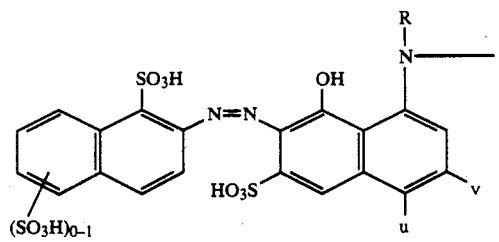 (I)

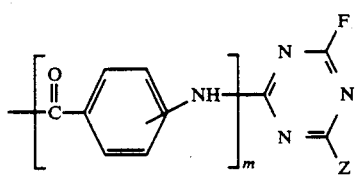

in which
u and v=H or SO$_3$H and u≠v,
R=H or C$_1$-C$_4$-alkyl, it being possible for the alkyl groups to be optionally substituted by OH, halogen, SO$_3$H or OSO$_3$H,
m=0 or 1

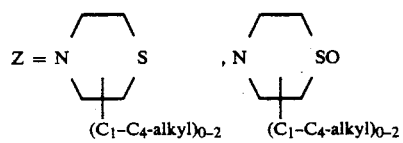

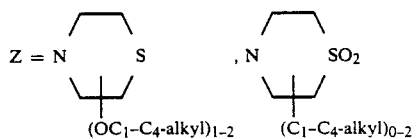

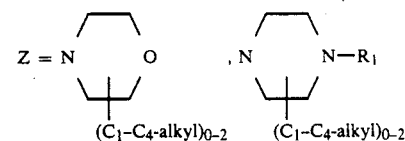

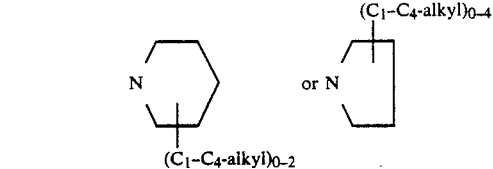

in which R$_1$=H or C$_1$-C$_6$-alkyl which is optionally substituted by water-solubilizing substituents.

Suitable substituents for R$_1$ are in particular OH, OSO$_3$H, SO$_3$H, COOH. A preferred substituent R$_1$ is hydroxyethyl.

Preferred dyestuffs are those having Z=

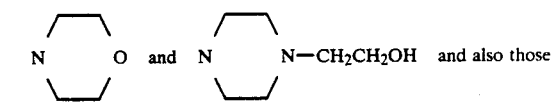 and also those based on 2-aminonaphthalene-1-sulphonic acid, 2-aminonaphthalene-1,5-disulphonic acid and 2-aminoaphthalene-1-6-disulphonic acid. Particular preference is given to dyestuffs where m=0. Very particular preference is given to dyestuffs of the formulae

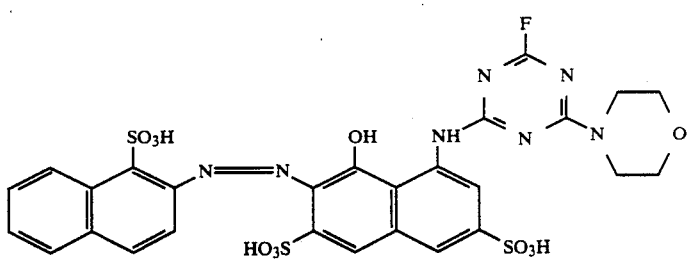 (II)

and

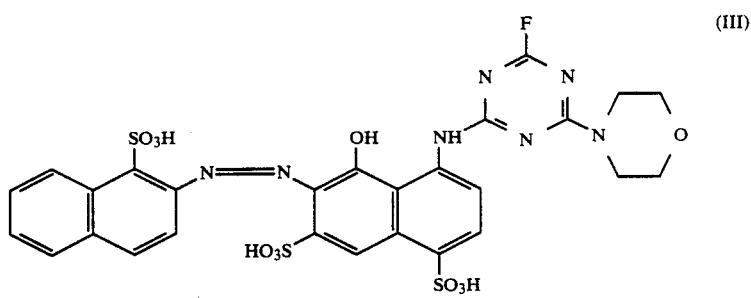 (III)

The dyestuffs are suitable for dyeing and printing hydroxyl- and amido-containing materials, in particular cellulose materials.

The novel fibre-reactive azo dyestuffs are characterized by a high reactivity and a high degree of fixation.

The dyeings or prints on cellulose materials which are obtainable using these dyestuffs are characterized by a high fibre-dye bond stability and also by an excellent stability to oxidizing agents such as peroxide- or chlorine-containing detergents. They hydrolysis products which are formed in the process of dyeing or printing are readily washed off.

The dyestuffs according to the invention are accessible by preparation processes which are customary for the synthesis of reactive dyestuffs.

Thus, the novel dyestuffs can be prepared for example by the following methods:

1st step: Condensation of aminonaphtholdisulphonic acid with trifluorotriazine (=reaction product A)

2nd step: Condensation of difluorotriazinylaminonaphthol-disulphonic acid with the amine H—Z (=reaction product B)

3rd step: Diazotization of the diazo component and coupling with reaction product B.

A further way of preparing the dyestuffs consists in switching the reaction steps 2 and 3, that is the coupling with the reaction product A is carried out as the 2nd step and the product is not reacted with the amine H—Z until after this step as the 3rd step.

A further process consists of condensing the conventionally prepared dyestuff of the formula

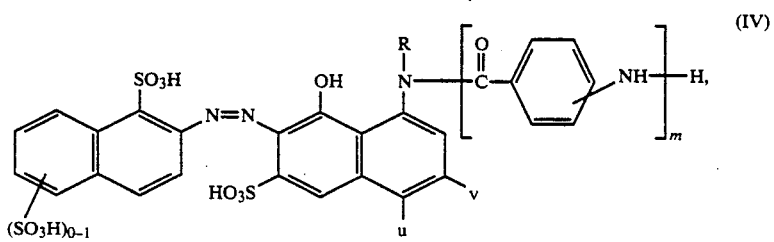

(IV)

in which m, R, u and v have the above mentioned meaning, with trifluorotriazine and then reacting the product with the amine H—Z.

Suitable examples of amines H—Z are morpholine, thiomorpholine, piperazine, N-hydroxyethylpiperazine, N-hydroxypropylpiperazine, piperidine, pyrrolidine, thiomorpholine-1,1-dioxide, 2,6-dimethylmorpholine.

Suitable diazo components are in particular 2-aminonaphthalene-1-sulphonic acid, 2-aminonaphthalene-1,5-disulphonic acid and 2- aminonaphthalene-1,6-disulphonic acid.

The formulae given are those f the free acids. The preparation generally give the salts, in particular the alkali metal salts such as sodium, potassium or lithium salts.

The present invention further provides the coupling components underlying the dyestuffs of the formula I and have the formula

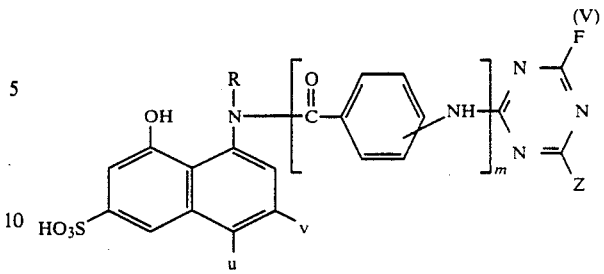

(V)

in which the radicals mentioned have the meanings given above.

EXAMPLE 1

31.9 g of 1-hydroxy-[-aminoaphthalene-3-3,6-disulphonic acid are dissolved in 400 of water under neutral conditions. 8.8 ml of trifluorotriazine are added to the mixture at 0°-5° C., and the pH of the solution is kept at 4.0°-4.5 by adding 20% strength sodium carbonate solution. After 5 minutes, 9 g of morpholine are added and the pH of the solution is kept at 7 with 20% strength sodium carbonate solution. After 15 minutes at 10° C., the reaction is completed. The solution of the compound of the formula

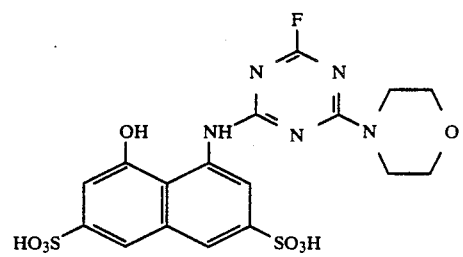

thus obtained can be converted directly into a brilliant red azo reactive dyestuff by the following method:

A diazonium salt suspension obtained in a conventional manner by diazotization of 22.3 g of 2-aminomaphthalene-1-sulphonic acid is added at 0°-5° C. to the reaction product obtained. Simultaneously, the pH is kept at 8.3 using 20% strength sodium carbonate solution an the coupling is completed. The dyestuff of the formula

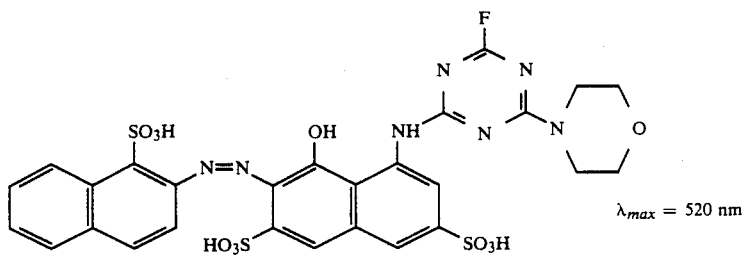

$\lambda_{max} = 520$ nm is salted out, filtered off with suction, dried and ground. The red dyestuff powder is readily soluble in water.

Using an application process which is customary for reactive dyestuffs, bright bluish red dyeings are thus obtained on cotton.

EXAMPLE 2

If the 1-hydroxy-8-aminoaphthalene-3,6-disulphonic acid of Example 1 is replaced by the equivalent amount of 1-hydroxy-8-aminoaphthalene-3,5-disulphonic acid and the procedure is otherwise as described in Example 1, the dyestuff of the formula

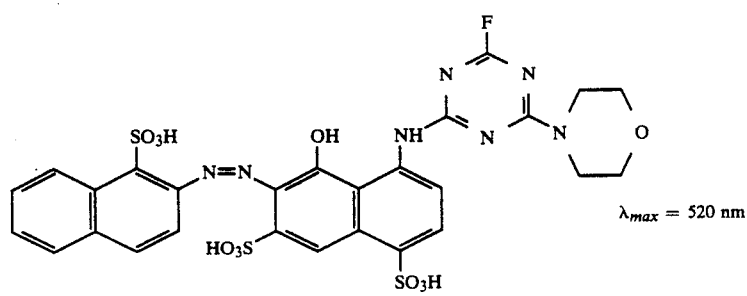

$\lambda_{max} = 520$ nm is obtained, which also dyes cotton in bright bluish red shades in an application process which is customary for reactive dyestuffs.

EXAMPLE 3

If the diazonium salt suspension prepared in a conventional manner by diszotization of 2-aminoaphthalene-1,5-disulphonic acid is added to the solution of the coupling component prepared in Example 1 and the procedure is otherwise as described in Example 1, the dyestuff of the formula

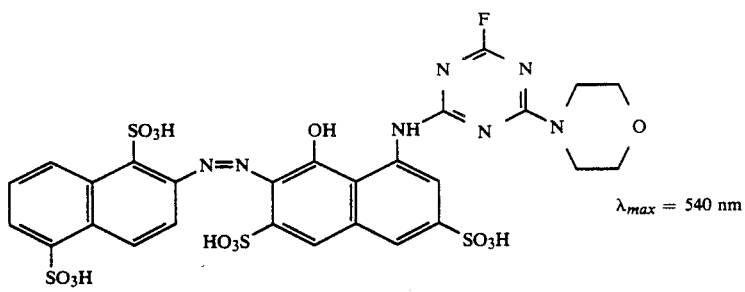

$\lambda_{max} = 540$ nm is obtained, which also dyes cotton in bright bluish red shades in an application process which is customary for reactive dyestuffs.

EXAMPLE 4

If the diazonium salt suspension prepared in a conventional manner by diazotization of 2-aminoaphthalene-1,5-disulphonic acid is added to the coupling component described in Example 2 and the procedure is otherwise as described in Example 2, the dyestuff of the formula

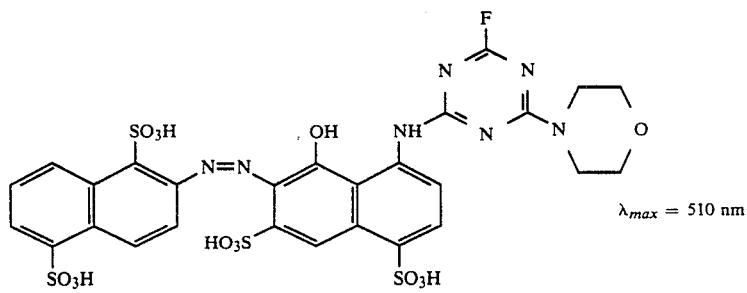

$\lambda_{max} = 510$ nm is obtained, which also dyes cotton in bright red shades in an application process which is customary for reactive dyestuffs.

EXAMPLE 5

If the 2-amino-1-naphthalenesulphonic acid of Examples 1 and 2 is replaced by 2-amino-1,6-naphthalenedisulphonic acid and the procedure is otherwise as described in the examples, the dyestuffs of the formulae

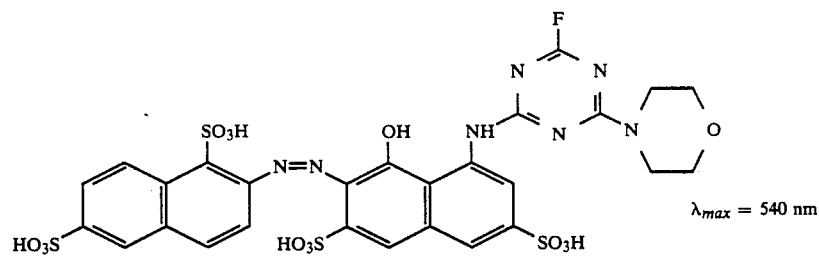

$\lambda_{max} = 540$ nm and

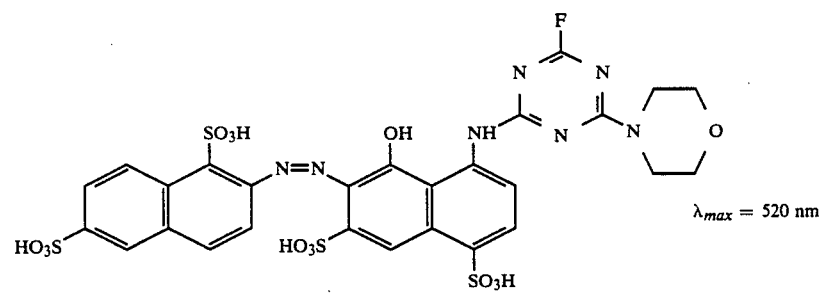

$\lambda_{max} = 520$ nm are obtained. These dyestuff dye cotton in bright bluish red shades by using an application process which is customary for reactive dyestuffs.

EXAMPLE 6

If the morpholine which was used for the preparation of the coupling components in each of Examples 1-5 is replaced by the corresponding amounts of piperazine, N-hydroxyethylpiperazine, piperidine or pyrrolidine, red dyestuffs having excellent properties are likewise obtained.

EXAMPLE 7

43.8 g of 1-hydroxy-8-(4-aminobenzoylamino)-naphthalene-3,6-disulphonic acid are dissolved in 400 ml of water under neutral conditions. 8.8 ml of trifluorotriazine are added to the mixture at 0°-5° C., and the pH of the solution is kept at 4.0-4.5 by adding 20% of strength sodium carbonate solution. After 5 minutes, 9 g of morpholine are added and the pH is adjusted to 7 using 20% strength sodium carbonate solution. After 15 minutes at 10° C., the reaction is completed. The solution of the compound of the formula

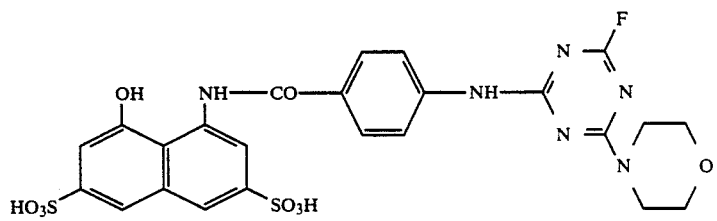

thus obtained can be converted directly into a brilliant red azo reactive dyestuff by the following method: A diazonium salt suspension prepared in a conventional manner by diazotization of 30.3 g of 2-amino-naphthalene-1-5-disulphonic acid is added at 10°-15° C. to the reaction product obtained. Simultaneously, the pH of the mixture is kept at 7.5 using 20% strength sodium carbonate solution and the coupling is completed. The dyestuff of the formula

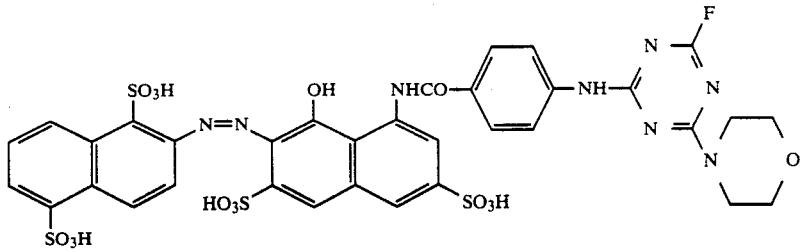

is salted out, filtered off with suction, dried and ground. The red dyestuff powder is readily soluble in water. Using an application process which is customary for reactive dyestuffs, bright bluish red dyeings are thus obtained on cotton.

EXAMPLE 8

If the 1-hydroxy-8-(4-aminobenzoylamino)naphthalene-3,6-disulphonic acid of Example 7 is replaced by the equivalent amount of 1-hydroxy-8-(4-aminobenzoylamino)naphthalene-3,5-disulphonic acid and the procedure is otherwise as described in Example 7, the dyestuff of the formula is obtained, which also dyes cotton in bright bluish red shades by using an application process which is customary for reactive dyestuffs.

EXAMPLE 9

If the 2-aminonaphthalene-11,5-disulphonic acid of Examples 7 and 8 is replaced by 2-aminonaphthalene-1,6-disulphonic acid and the procedure is otherwise as described in the examples, the dyestuffs of the formulae

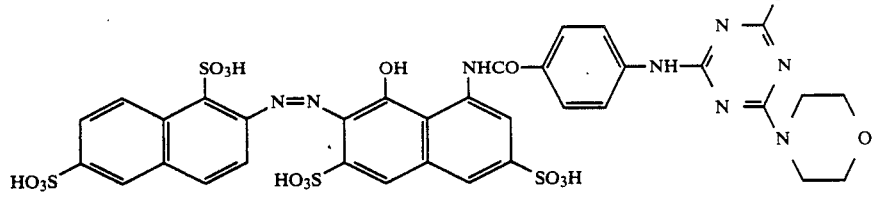

and

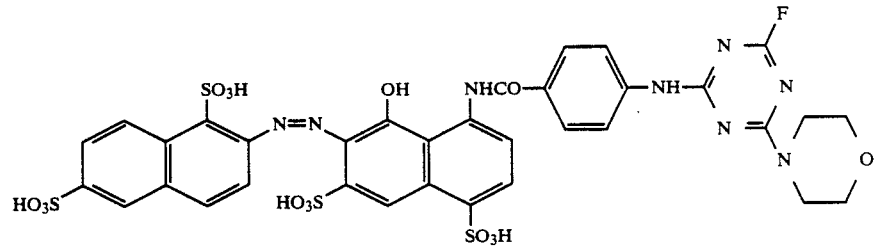

are obtained. These dyestuffs dye cotton in bright bluish red shades by using an application process which is customary for reactive dyestuffs.

EXAMPLE 10

If the 2-aminonaphthalene-1,5-disulphonic acid of Examples 7 and 8 is replaced by 2-amino-1-naphthalenesulphonic acid and the procedure is otherwise as described in the examples, the dyestuffs of the formulae

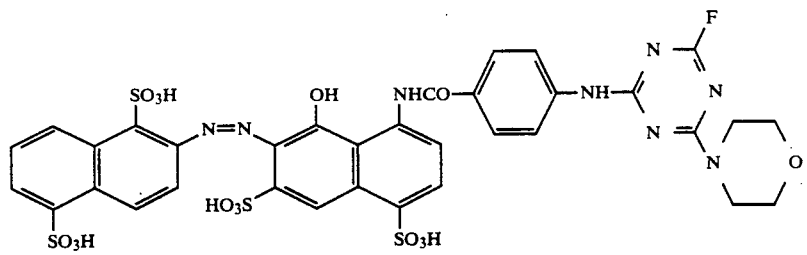

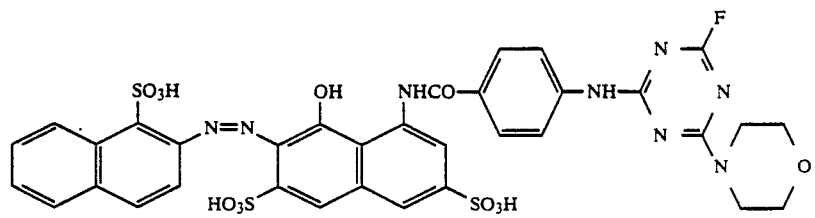

and

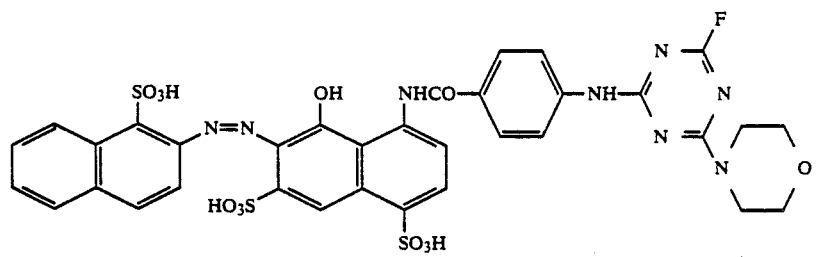

are obtained which also dye cotton in bright bluish red shades by using an application process which is customary for reactive dyestuffs.

EXAMPLE 11

If the morpholine which was used for the preparation of the coupling component in each of Examples 7–10 is replaced by the corresponding amounts of piperazine, N-hydroxyethylpiperazine, piperidine or pyrrolidine, red dyestuffs having excellent properties are likewise obtained.

EXAMPLES 12–25

Analogously to Example 1, further interesting coupling components can be prepared by using the naphthalene-sulphonic acids and amines listed in the following table:

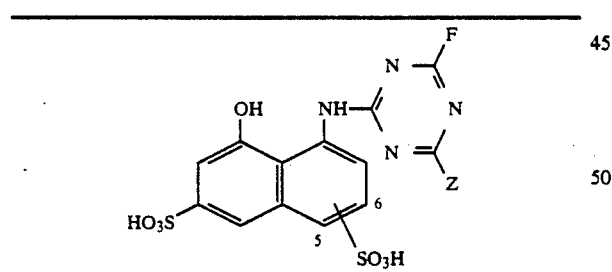

| No. | Position of the sulphonic acid group | Z |
|---|---|---|
| 12 | 6 | —N⌒S⌒ |
| 13 | " | —N(CH(CH₃)CH₂)₂O |

-continued

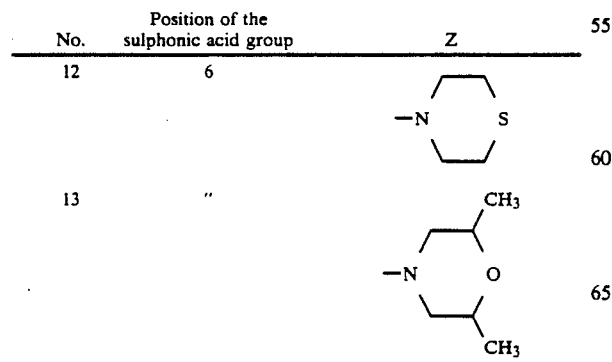

| No. | Position of the sulphonic acid group | Z |
|---|---|---|
| 14 | " | —N⌒SO⌒ |
| 15 | " | —N⌒SO₂⌒ |
| 16 | " | —N(CH(CH₃)CH₂)₂S |
| 17 | 6 | —N⌒S⌒ with OCH₂CH₃ |
| 18 | " | —N(CH(CH₃)CH₂)₂S |

-continued

[Structure: naphthalene with OH, NH-C(=NF)-N=C(-N)-Z guanidine-triazine system, HO3S at position 6, SO3H at position 5]

| No. | Position of the sulphonic acid group | Z |
|---|---|---|
| 19 | " | —N(CH(CH3)CH2)2SO2 (bis(isopropyl) with SO2 bridge) |
| 20 | 5 | —N(CH(CH3)CH2)2SO2 |
| 21 | " | —N(CH2CH2)2S (thiomorpholine) |
| 22 | " | —N(CH(CH3)CH2)2O |
| 23 | " | —N(CH2CH2)2SO2 |
| 24 | " | —N(CH(CH3)CH2)2S |
| 25 | " | —N(CH(CH3)CH2)2S |

EXAMPLE 26–55

By using the coupling components prepared in Examples 12–25, further important dyestuffs can be prepared using the diazo components listed in the following table D—N=N—K
K = coupling component

| No. | D | K = coupling component from | Hue |
|---|---|---|---|
| 26 | [naphthalene with SO3H, CH3] | Example 12 | bluish red |
| 27 | " | Example 13 | " |
| 28 | " | Example 14 | " |
| 29 | " | Example 15 | " |
| 30 | " | Example 16 | " |
| 31 | " | Example 17 | " |
| 32 | " | Example 18 | " |
| 33 | " | Example 19 | " |
| 34 | " | Example 20 | red |
| 35 | " | Example 21 | " |
| 36 | " | Example 22 | " |
| 37 | " | Example 23 | " |
| 38 | " | Example 24 | " |
| 39 | " | Example 25 | " |
| 40 | [naphthalene with SO3H, CH3, SO3H at 5] | Example 12 | bluish red |
| 41 | " | Example 13 | " |
| 42 | " | Example 15 | " |
| 43 | " | Example 21 | red |
| 44 | " | Example 23 | " |
| 45 | " | Example 24 | " |
| 46 | [naphthalene with SO3H, CH3, HO3S at 6] | Example 12 | bluish red |
| 47 | " | Example 13 | " |
| 48 | " | Example 15 | bluish red |
| 49 | " | Example 16 | " |
| 50 | " | Example 18 | " |
| 51 | " | Example 19 | " |
| 52 | " | Example 21 | red |
| 53 | " | Example 22 | " |
| 54 | " | Example 23 | " |
| 55 | " | Example 24 | " |

We claim:
1. An azo dyestuff of the formula

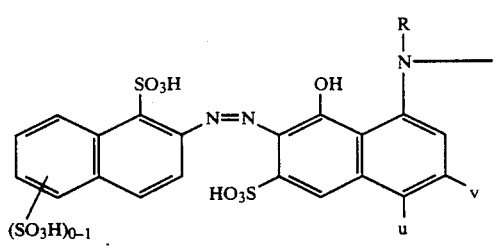

-continued

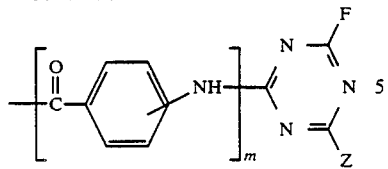

in which
u and v=H or SO$_3$H and u≠v,
R=H, unsubstituted C$_{1-C4}$-alkyl or C$_1$-C$_4$-alkyl substituted by OH, halogen, SO$_3$H or OSO$_3$H,
M=O and

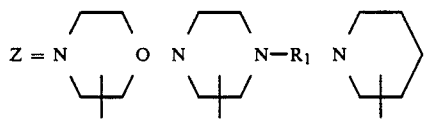

in which R$^1$—H, unsubstituted C$_1$-C$_6$-alkyl or C$_1$-C$_6$-alkyl substituted by OH, OSO$_3$H, SO$_3$H or COOH.

2. A dyestuff according to claim 1 where

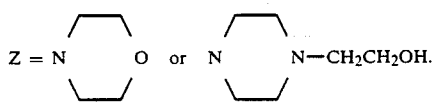

3. A dyestuff of the formula

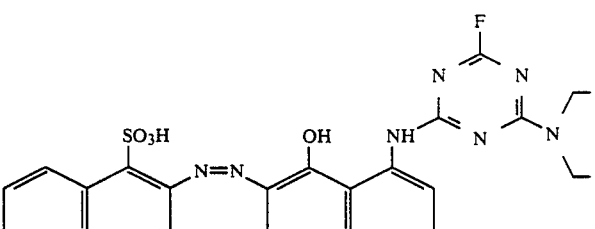

4. A dyestuff of the formula

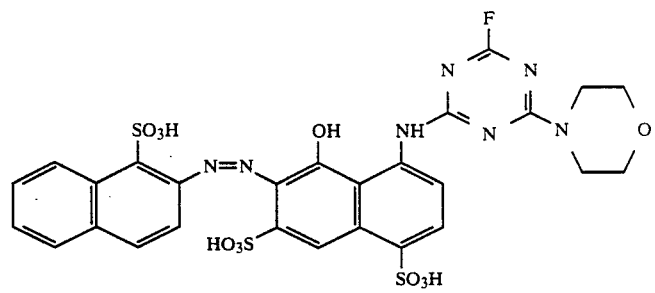

5. A dyestuff according to claim 1 of the formula

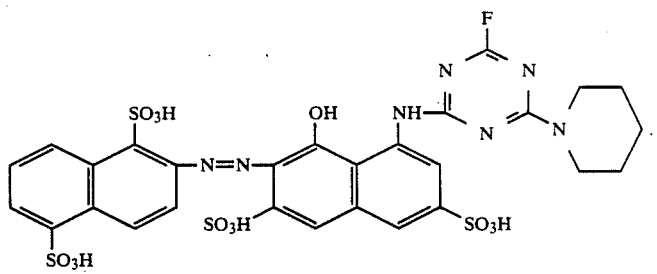

6. A dyestuff according to claim 1 of the formula

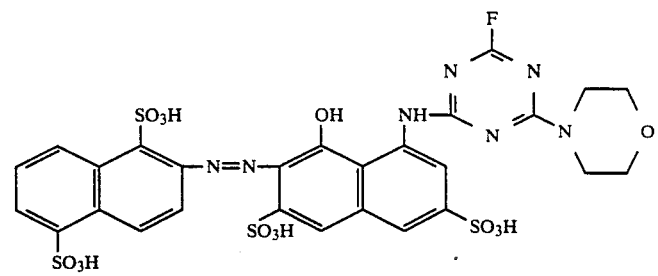

7. A dyestuff according to claim 1 of the formula

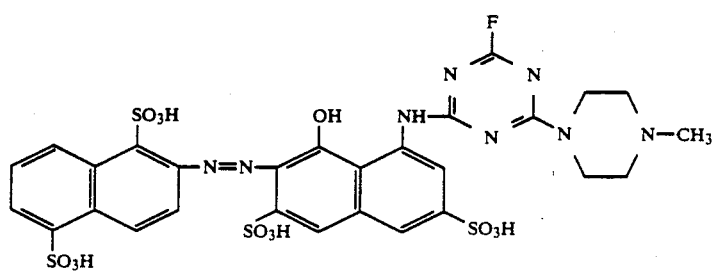
* * * * *

UNITED STATES PATENT AND TRADEMARK OFFICE
CERTIFICATE OF CORRECTION

PATENT NO. : 4,988,803
DATED : January 29, 1991
INVENTOR(S) : STOHR, et al

It is certified that error appears in the above-identified patent and that said Letters Patent is hereby corrected as shown below:

Col. 15, line 14     Delete " M=O " and substitute -- m=O --

Col. 15, lines 15-19     Delete "  " and substitute

--  --

Col. 16, line 10-19     Delete " 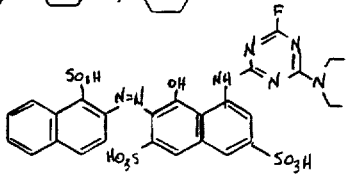

and substitute

-- 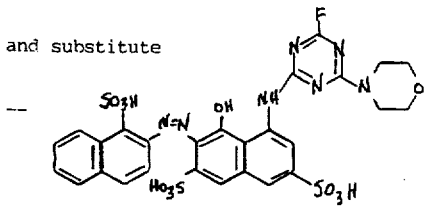 --

Signed and Sealed this

Sixteenth Day of February, 1993

*Attest:*

STEPHEN G. KUNIN

*Attesting Officer*     *Acting Commissioner of Patents and Trademarks*